(12) United States Patent
Dryer et al.

(10) Patent No.: US 8,221,766 B2
(45) Date of Patent: *Jul. 17, 2012

(54) USE OF PLANT EXTRACTS TO PREVENT AND/OR REDUCE THE SIGNS OF SUBJECTIVE DISCOMFORT AND/OR IRRITATION IN THE TOPICAL APPLICATION OF COSMETIC PRODUCTS

(75) Inventors: Laurence Dryer, Butler, NJ (US); Dmitri Ptchelintsev, Jersey City, NJ (US)

(73) Assignee: Avon Products, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/021,024

(22) Filed: Dec. 22, 2004

(65) Prior Publication Data

US 2006/0147407 A1    Jul. 6, 2006

(51) Int. Cl.
*A61K 35/00* (2006.01)
(52) U.S. Cl. .................................. 424/195.18; 424/401
(58) Field of Classification Search .................. 424/401, 424/195.18, 196.18
See application file for complete search history.

(56) References Cited

U.S. PATENT DOCUMENTS

| | | | | |
|---|---|---|---|---|
| 4,931,277 A | * | 6/1990 | Fontaine et al. | ............... 424/760 |
| 5,468,492 A | * | 11/1995 | Szaloki et al. | ................. 424/752 |
| 5,770,222 A | | 6/1998 | Unger et al. | |
| 5,834,513 A | | 11/1998 | Ptchelintsev et al. | |
| 5,847,003 A | | 12/1998 | Ptchelintsev et al. | |
| 5,993,833 A | | 11/1999 | De Lacharriere et al. | |
| 6,143,303 A | | 11/2000 | Janakiram et al. | |
| 6,146,636 A | * | 11/2000 | Breton et al. | ................. 424/765 |

FOREIGN PATENT DOCUMENTS

| | | | |
|---|---|---|---|
| JP | 2001-220320 A | * | 8/2001 |
| JP | 200287939 A | * | 3/2002 |
| JP | 2002087939 A | | 3/2002 |
| WO | WO 00/67767 | * | 11/2000 |
| WO | WO 00/67767 A1 | | 11/2000 |

OTHER PUBLICATIONS

Nakaguchi et al. JP02002087939A, Mar. 27, 2002, Abstract.*
Sokolnicka, I., et al. Immunostimulatory effects of water-soluble extracts of poplar buds and leaves and their polyphenolic compounds, Int. J. Immunotherapy, 1994, X(2) 83-88.*
Thongsaard, W. et al. Neuroscience Letters 329 (2002) 129-132.*
Nakaguchi, O. et al, "Hair-growing agent composition", JP 2001-220320 A, (Aug. 14, 2001), machine translation.*
Rujjanawate, C. et al., "Analgesic effect of *Sapindus rarak* pericarp extract", J. Trop. Med. Plants. vol. 5, No. 1 (Jun. 2004), pp. 11-14.*

* cited by examiner

*Primary Examiner* — Gina C Yu
(74) *Attorney, Agent, or Firm* — Joan M McGillycuddy; Charles J. Zeller; David M. Joyal

(57) ABSTRACT

The present invention describes compositions and methods for treating, preventing and improving the appearance of skin, particularly, treating, preventing, ameliorating, reducing and/or eliminating skin irritation, inflammation, and/or the signs of visible or subjective discomfort, wherein the compositions include natural plant constituents that inhibit at least one cytokine. The plant extracts are preferably derived from *Populus nigra, Rhinacanthus nasutus, Sapindus rarak,* and *Thumbergia laurifolia,* and any combinations thereof. The compositions are preferably applied to the skin, or are delivered by directed means, to a site in need thereof.

12 Claims, No Drawings

USE OF PLANT EXTRACTS TO PREVENT AND/OR REDUCE THE SIGNS OF SUBJECTIVE DISCOMFORT AND/OR IRRITATION IN THE TOPICAL APPLICATION OF COSMETIC PRODUCTS

FIELD OF THE INVENTION

The present invention relates to the novel use of natural plant materials, or extracts derived therefrom, in cosmetic products for the face and body. More particularly, the present invention relates to topical compositions that improve the appearance of skin, especially by alleviating skin irritation, with the topical compositions having at least one natural plant material, or extract derived therefrom, that inhibits I-CAM, IFN-γ, IL1-β, IL12, IL6, IL8, IL2, IP10, TNF-α and TNFr2. Still more particularly, the present invention relates to methods for using the topical compositions of the present invention. The invention further relates to methods of delivery for such compositions so as to allow the active plant constituents to more readily penetrate the target area and treat, including prevent, reduce, ameliorate, and/or eliminate skin irritation, and to improve the aesthetic appearance of skin.

BACKGROUND OF THE INVENTION

Active ingredients derived from plants have over time been employed in topical compositions for a wide variety of medicinal, therapeutic and cosmetic purposes. Such actives can be obtained from various parts of a plant such as seeds, leaves, roots, bark, flowers, cones, stems, rhizomes, callus cells, protoplasts, organs and organ systems, and meristems. Active ingredients are incorporated in such compositions in a variety of forms. Such forms include a pure or semi-pure component, a solid or liquid extract or derivative, or solid plant matter. Plant matter may be minced, ground, crushed or otherwise physically modified for incorporation into a composition.

A problem commonly encountered when using an active ingredient derived from a plant or plant part is the relatively low level at which they are naturally present. Such low levels frequently require relatively large amounts of plant leaf/tissue or seed be processed in order to obtain desired or useful quantities of active ingredients. For rare plants or plant parts, such large amounts may be unavailable or difficult to obtain.

Currently, a wide variety of topically applied pharmaceutical and cosmetic products are in commercial use. For example, there is active contemporary interest in the cosmetics industry to develop products that may be applied topically to the skin that provide anti-aging, hydrating, and/or skin texturing benefits. Cosmetic products that enhance the appearance of skin are increasingly in demand. Consumers are interested in mitigating or delaying the signs of chronologically, hormonally and/or photo-aged skin, such as fine lines, wrinkles, dry skin, and sagging skin. During the aging process, the complexion of the skin, i.e., the color and appearance of the skin, deteriorates slowly from intrinsic aging and/or exposure to sunlight. Cosmetic surgery can be used as a treatment for aged skin, but such treatment is costly and carries the risks normally associated with anesthesia and surgery. Alternatively, cosmetic products that are able to provide anti-aging or other skin-care benefits are highly desired by consumers. However, one problem that arises with pharmaceutical and cosmetic topically applied products is that the active ingredient or ingredients are often irritating to the skin. This side effect may limit the use of, or the concentration of, certain cosmetic or pharmaceutical active ingredients.

The number of cosmetic skin care products is steadily increasing. Commonly, such products contain organic acids or other materials as active ingredients. Such active ingredients include, for example, hydroxylated acids and their derivatives, such as omega-hydroxy acids (i.e., undecanoic acid), α-hydroxy acids (i.e., lactic, glycolic, citric), β-hydroxy acids (i.e., salicylic, 5-n-octanoylsalicylic), and retinoids (i.e., retinoic acids, retinol). It is known that these active ingredients have a significant disadvantage in that they frequently are associated with consumer skin irritation or discomfort characterized by burning, smarting, itching or sensation of tightness after application. There remains a general need in both the cosmetics industry and pharmaceutical industry for topically applied products containing various active ingredients that are effective without producing the undesirable side effect of skin irritation. It is known that a significant number of consumers have sensitive skin or are susceptible to allergic skin reactions when topically applied products are used. For example, products having certain surfactants, preservatives, fragrances and the like, as well as active ingredients, have skin-irritant characteristics.

More particularly, in view of the previous discussion of demands and limitations in the cosmetics industry, there remains a need for topically applied, cosmetic compositions that have skin benefits without skin irritation as a side effect using natural ingredients as active components.

Methods for treatment of skin prone to irritation or skin inflammation are known. For example, U.S. Pat. No. 5,993,833 is directed to methods for treatment of sensitive skin comprising administering a composition having an antagonist compound. U.S. Pat. No. 6,143,303 is directed to an anti-inflammatory, analgesic composition comprising an extract of the plants *Dodonaea petiolaris* and *dodonaea viscosa*.

In spite of the various pharmaceutical and cosmetic products on the market that are topically applied to skin, there remains a need for effective topically applied compositions that incorporate natural plant materials, or extracts derived therefrom, or synthesized forms of natural plant extracts to provide an improved aesthetic appearance to the skin, especially skin irritation, or to achieve the benefits of active ingredients contained in the composition with mitigation or elimination of irritant side effects occasioned by the use such actives.

Safe, effective and new components of compositions to treat, prevent, reduce, inhibit, and/or improve the skin irritation and/or discomfort, would be advantageous for the formulation of treatments and products for the skin. As described herein, novel and beneficial methods and compositions, as well as their mode of action, for the treatment of skin irritation and the like, as well as for personal care products for the skin, are provided by the present invention.

SUMMARY OF THE INVENTION

The present invention provides compositions and methods comprising natural plant materials, or extract derived therefrom, newly found to be effective to treat, including prevent, reduce, ameliorate, and/or eliminate skin irritation, inflammation, and/or visible or subjective signs of discomfort, and to improve the aesthetic appearance of skin.

It is an aspect of the present invention to provide topical compositions having a natural plant material, or extracts derived therefrom, from at least one plant, or blends of plant materials, preferably natural plant extracts. In particular, the present invention is directed to natural plant materials, or extracts derived from at least one of the following plants:

*Populus nigra, Rhinacanthus nasutus, Sapindus rarak,* and *Thumbergia laurifolia*. These natural plant materials, or extracts, have been newly found to provide treatment for skin irritation, inflammation, and other signs of visible or subjective discomfort, by inhibiting proteins (referred to as cytokines) that modulate inflammation in the skin.

It is another aspect of the present invention to provide topical compositions having a natural plant material, or extracts derived therefrom, or blends of plant-derived materials or extracts, that inhibit I-CAM, IFN-γ, IL1-β, IL12, IL6, IL8, IL2, IP10, TNF-α and TNFr2 in a cosmetically or dermatologically acceptable vehicle.

It is still another aspect of the present invention to provide a topical composition that delivers a natural plant material, or extract therefrom, or blends of plant-derived materials or extracts, together with an effective level of a cosmetic, dermatologic, or pharmaceutic active ingredient.

It is a further aspect of the present invention to provide methods for topically applying such compostions.

It is a still further aspect of the present invention to provide methods of improving the appearance of skin, including treating skin symptoms and conditions relating to skin irritation, inflammation, and/or visible or subjective discomfort, and remediating the effects of aging, by topically applying the compositions of the invention to the skin.

It is to be understood that, as used herein, the terms treating and treatment include and encompass preventing, reducing, ameliorating, improving, alleviating, and/or eliminating the dermatological effects of aging, with particular regard to conditions and symptoms relating to skin irritation, inflammation, discomfort, and the like. The present compositions and methods are also suitable for use in treating, as defined above, dermatological conditions of the skin in numerous areas of the body, including, without limitation, the face, forehead, lips, neck, arms, hands, legs, knees, feet, chest, back, groin, buttocks, and the like.

The present compositions alleviate signs of irritation, including, but not limited to: erythema, psoriasis, edema, hyper/hypopigmentation, wheeling, blotchiness, uneven skin tone, scaling, flaking, itching, burning, stinging, tingling, numbing, acne, wind irritation, temperature irritation, smoke irritation, and chemical irritation.

In accordance with this invention, compositions comprising the natural plants materials, or extracts derived therefrom, may further include, without limitation, topically applied sunscreens, anti-oxidants, anti-inflammatories, cosmetics, including makeups, anti-aging formulations, e.g, creams for fine lines and/or wrinkles, topicals, skin permeants antiperspirants, deodorants and the like. Also in accordance with this invention, ingredients, components, or compounds that are formulated in such compositions in a variety of product forms, e.g., liposomes, and the like, are encompassed, particularly for topical administration.

Another aspect of the present invention provides that such compositions are preferably delivered by, but not limited to, the use of targeted delivery systems, for example, liposomes, microspheres, transdermal patches, and the like, so that the natural plant materials, or extracts derived therefrom, can more readily penetrate the skin layer of the area of application, e.g., face or neck. Compositions comprising plant constituents, including liposome formulations, are preferably administered topically.

Another aspect of this invention provides a method of reducing, preventing, treating, or ameliorating skin irritation, inflammation, or visible or subjective signs of discomfort in the skin, comprising: applying a composition comprising a natural plant material, or extract derived therefrom, to the skin in an amount effective to inhibit a cytokine, thereby treating, preventing, reducing, ameliorating, or eliminating skin irritation, inflammation, and/or visible or subjective signs of discomfort.

Another aspect of the present invention relates to a method of improving the aesthetic appearance of skin and comprises applying to the skin the compositions of the present invention.

Further aspects, features and advantages of the present invention will be better appreciated upon a reading of the detailed description of the invention.

DESCRIPTION OF THE INVENTION

The present invention provides novel compositions and methods comprising natural plant materials, or extracts derived therefrom, newly found to be effective to treat, including prevent, reduce, ameliorate, inhibit, alleviate, and/or eliminate signs and results relating to skin irritation and/or to improve the aesthetic appearance of skin.

More specifically, the natural plant materials (also referred to as extracts, components, active agents, constituents, ingredients, reagents, substances, or compounds herein) of this invention are obtained from at least one of the following plants: *Populus nigra, Rhinacanthus nasutus, Sapindus rarak,* and *Thumbergia laurifolia*. These plant materials have been newly found to provide treatment for skin irritation, inflammation, and/or visible or subjective signs of discomfort, and other signs of dermatological aging by inhibiting cytokines in the skin. These natural plant materials, or extracts derived therefrom, have been newly determined to be effective agents in compositions and methods for treatment.

According to the present invention, yet without wishing to be bound by theory, the natural plant materials, or extracts described herein, exert their effectiveness by preferably inhibiting the cytokines that mediate inflammation. More specifically, the natural plant materials inhibit I-CAM, IFN-γ, IL1-β, IL12, IL6, IL8, IL2, IP10, TNF-α, and TNFr2 (see Example 2). The result of inhibiting these cytokines is the improvement or reduction of inflammation, especially skin irritation and/or visible or subjective signs of discomfort, thereby treating the undesireable side effects of irritated skin, which can also make skin appear older.

The present invention in its broadest view encompasses the use in any topical cosmetic, dermatological, or pharmaceutical composition of any convenient natural plant or ingredient that inhibits I-CAM, IFN-γ, IL1-β, IL12, IL6, IL8, IL2, IP10, TNF-α, and TNFr2 to alleviate or treat skin irritation, inflammation, and/or any visible or subjective signs of discomfort in the skin.

The present invention also provides for compositions to improve the aesthetic appearance of skin, including ameliorating or treating the effects of aging. These benefits are manifest by one or more of the following: improvement in skin tone, radiance, clarity and/or tautness; improvement in skin firmness, plumpness, suppleness, and/or softness; improvement in skin texture and/or promotion of retexturization; improvement in skin barrier repair and/or function; improvement in appearance of skin contours; restoration of skin luster and/or brightness; improvement in communication among skin cells; increase in skin cell metabolism decreased by aging and/or menopause; improvement in skin moisturization; enhancement of skin thickness; reducing skin sensitivity; and increase in skin resiliency. By reducing irritation and inflammation in the skin, the natural plant materials, or extracts derived therefrom, may also treat, prevent, reduce, ameliorate, and/or eliminate aesthetically displeasing wrinkles, fine lines, scaling, peeling, flaking, redness, dryness, etc. that can arise from aging.

The present invention also provides for compositions that provide an anti-aging benefit. The compositions have an effective amount of one or more ingredients which, when applied to human skin, prevent, treat and/or ameliorate the various signs of aging at the area or portion of skin to which they are applied. In particular, the present invention provides compositions and methods for treating skin to prevent, inhibit, reduce and/or ameliorate the signs of dermatological aging due to, for example, chronological aging, hormonal aging, and/or photoaging. Such signs of aging include, but are not limited to skin fragility; loss of collagen and/or elastin; skin atrophy; appearance and/or depth of lines and/or wrinkles, including fine lines; skin discoloration, including dark eye circles; skin sagging; skin fatigue and/or stress, e.g., skin breakout due to environmental stress, such as pollution and/or temperature changes; skin dryness; skin flakiness; cellular aging; loss of skin tone, elasticity and/or luster; loss of skin firmness; poor skin texture; loss of skin elasticity and/or resiliency; and thin skin.

To improve the aesthetic appearance of skin, these compositions have at least one of the natural plant materials, or extracts derived therefrom, or synthesized forms of the natural plant extracts of the present invention; namely, *Populus nigra, Rhinacanthus nasutus, Sapindus rarak,* and *Thumbergia laurifolia*. Also preferably, these compositions also have one or more cosmetically active agents as known in the cosmetic field, including, but not limited to, the cosmetic agents enumerated herein, that provide one or more of the above-identified skin appearance benefits.

Skin irritation may result from a variety of physical or chemical factors, including environmental factors such as exposure to wind, heat or cold, air pollutants, and cigarette smoke. Cosmetic and pharmaceutical products may have ingredients or combinations of ingredients that produce visible skin irritation as a side effect. Susceptibility to skin irritation may vary from individual to individual, and frequently limits the use of certain products or the use of concentrations of active ingredients that might produce more advantageous results at higher levels but for the production of skin irritation as a side-effect. Skin irritation symptoms or conditions include, but are not limited to, erythema, psoriasis, edema, hyper-pigmentation, hypo-pigmentation, acne, wheeling, blotchiness, uneven skin tone, scaling, flaking, itching or pruritus, tightness, burning, prickling, stinging, tingling, numbing, wind irritation, temperature irritation, smoke irritation, chemical irritation, or any combinations thereof.

Cosmetic, dermatological and pharmaceutical products commonly have an active agent or agents that produce skin irritation. Examples of active agents having skin irritation as a side effect include, but are not limited to, hydroxylated acids and their derivatives, $\alpha$-hydroxy acids (i.e., lactic, glycolic, citric, malic, tartaric, mandelic, gluconic, methyl lactic, phenyl lactic, atrolactic, glyceric, benzilic, z-hydroxyheptanoic, z-hydroxyoctanoic and any combinations thereof), $\beta$-hydroxy acids (i.e., salicylic, 5-n-octanoylsalicylic and other derivatives of salicylic), retinoids (retinoic acid and its derivatives; retinol and its esters); anthralins (i.e., dioxyanthranol), anthranoids, peroxides (i.e., benzoyl peroxide), minoxidil, lithium salts, antimetabolites, vitamin D and its derivatives, hair dyes or colorants (i.e., para-phenylenediamine and its derivatives; aminophenols), alcoholic perfuming solutions (i.e., perfumes; toilet waters; aftershaves; deodorants), antiperspirant agents (i.e., some aluminum salts), depilatory or hair permanent active agents (i.e., thiols), depigmentating agents (i.e., hydroquinone), and some insecticide active agents. If topical products had anti-irritant protection, it would be possible to increase the amount of the normal irritant active agent (i.e., AHA or BHA) in the product without producing unpleasant skin irritation or irritation side effects. The use of the present compositions makes it possible to improve the efficacy of cosmetic, dermatological or pharmaceutical products by increasing the concentration or amount of cosmetic, dermatological, or pharmaceutical active agent as compared to the amount or concentration of such agent normally used.

It has now been found that the addition of natural plant materials, or extracts derived therefrom, which are antagonistic to I-CAM, IFN-$\gamma$, IL1-$\beta$, IL12, IL6, IL8, IL2, IP10, TNF-$\alpha$ and TNFr2 to topical cosmetic, dermatological, or pharmaceutical compositions, preferably compositions having skin-irritant ingredient(s), alleviates or even eliminates skin irritation.

Cytokines include compounds such as, for example, histamines or interleukins, that are inflammatory modulators. The use of one or more inhibitors or antagonists to these compounds in a cosmetic, dermatological or pharmaceutical topical product would alleviate skin inflammation.

The phrase "skin irritation" includes, but is not limited to, the visible and/or subjective irritation of skin, including but not limited to erythema, psoriasis, edema, hyper-pigmentation, hypo-pigmentation, acne, wheeling, blotchiness, uneven skin tone, scaling, flaking, itching, burning, stinging, tingling, numbing, wind irritation, temperature irritation, smoke irritation, and/or chemical irritation. The compositions of the present invention are also effective in treating subclinical irritation, i.e., where redness is not present, but where the skin is already compromised at a cellular level.

The one or more plant materials, preferably natural plant extracts, used in compositions of the present invention to inhibit cytokines for treatment of skin irritation include one or more extracts, or natural ingredients. These extracts or natural ingredients are preferably any one or more of the following: *Populus nigra, Rhinacanthus nasutus, Sapindus rarak,* and *Thumbergia laurifolia.*

For purposes of the invention, the natural plant material may be in any form including, but not limited to, the whole plant, a dried plant, a ground plant, an extract, a dried extract, a synthetic extract, or components and/or constituents found in, or isolated from, the plants, and/or portions of the plants, or extracts derived either directly or synthetically from the plants, or combinations thereof.

In one embodiment, the composition may have an extract derived from a natural plant material in an amount from about 0.0001% to about 50%, preferably from about 0.001% to about 20%, more preferably from about 0.01% to about 5%, and most preferably from about 0.05% to about 1%, based on the total weight of the composition, where the composition is useful in improving the condition and aesthetic appearance of skin.

The present invention provides, as one embodiment, compositions for treatment of skin irritation, inflammation, and/or discomfort having a cosmetically, dermatologically or pharmaceutically effective amount of at least one ingredient or extract derived from the above plant sources sufficient to inhibit I-CAM, IFN-$\gamma$, IL1-$\beta$, IL12, IL6, IL8, IL2, IP10, TNF-$\alpha$ and TNFr2 Preferably, such compositions also have a cosmetically, dermatologically or pharmaceutically acceptable vehicle. In addition, blends of such ingredients or extracts may conveniently be employed. Embodiments of the present invention may conveniently be employed to treat various skin irritation symptoms or conditions (i.e., erythema, psoriasis, edema, hyper-pigmentation, hypo-pigmentation, acne, wheeling, blotchiness, uneven skin tone, scaling, flaking, itching, burning, stinging, tingling, numbing, wind irritation, temperature irritation, smoke irritation, and chemical irritation).

In other embodiments of the present invention, compositions may have an active ingredient, or combination of active ingredients, in an amount that would normally produce skin irritation symptom or condition, but for the inclusion in such compositions of a cosmetically, dermatologically or pharmaceutically effective amount of one or more ingredients or extracts derived from the above plant sources sufficient to inhibit I-CAM, IFN-γ, IL1-β, IL12, IL6, IL8, IL2, IP10, TNF-α and TNFr2. Such extracts, or blends of extracts, and one or more active ingredients or combination of active ingredients in an amount that would normally produce skin irritation symptom or condition, are conveniently incorporated into a pharmaceutically or cosmetically acceptable vehicle in a form suitable for topical application.

Cosmetically, dermatologically or pharmaceutically acceptable vehicles that can be used in the present topical compositions include, but are not limited to, one or more aqueous systems, glycerins, $C_{1-4}$ alcohols, fatty alcohols, fatty ethers, fatty esters, polyols, glycols, vegetable oils, mineral oils, liposomes, laminar lipid materials, silicone oils, water or any combinations thereof.

In the present invention, the vehicle may be in the form of an aqueous phase, an oil phase, a gel, a wax-in-water emulsion, an oil-in-water emulsion, or a water-in-oil emulsion. The aqueous phase is a mixture of one or more water soluble or water dispersible ingredient, which can be liquid, semisolid or solid at room temperature (25° C.). The vehicle comprises or can be in the form of a suspension, dispersion or solution in water or an aqueous-alcoholic vehicle, which may contain a thickener or gellant. A person skilled in the art can select the appropriate product form, the ingredients contained therein, as well as the method for preparing it, on the basis of the knowledge that the skilled artisan possesses.

The composition may include an aqueous phase which may contain water or a mixture of water and at least one hydrophilic organic solvent such as an alcohol, especially a linear or branched lower monoalcohol containing from 2 to 5 carbon atoms, e.g., ethanol or propanol; a polyol, e.g., propylene glycol, sorbitol, glycerol, diglycerol, panthenol, or polyethylene glycol, and mixtures thereof. This aqueous phase may represent from 0.5 to 99.99 wt. % by weight of the composition.

When the composition of the invention is in the form of an emulsion, it can also optionally comprise a surfactant, preferably in an amount of from 0.1 to 30% and in particular from 1 to 20 wt. % by weight of the composition.

The composition can also comprise a film-forming polymer such as a polyurethane, a polyacrylic homopolymer or copolymer, a polyester, a hydrocarbon-based resin and/or a silicone resin. The polymers can be dissolved or dispersed in the cosmetically acceptable vehicle and optionally combined with a plasticizer.

The composition of the invention may also comprise an oil phase containing oil soluble or oil dispersible ingredients that are liquid at room temperature (25° C.) and/or oily or waxy substances that are solid at room temperature, such as waxes, semisolids, gums, and mixtures thereof. This oily phase may also contain organic solvents.

Suitable oily materials that are liquid at room temperature, often referred to as oils, include hydrocarbon-based oils of animal origin such as perhydrosqualene; hydrocarbon-based plant oils such as liquid triglycerides of fatty acids of 4 to 10 carbon atoms, for instance, heptanoic or octanoic acid triglycerides, or oils such as sunflower oil, corn oil, soybean oil, grapeseed oil, castor oil, avocado oil, caprylic/capric acid triglycerides, jojoba oil; linear or branched hydrocarbons of mineral or synthetic origin such as liquid paraffins and derivatives thereof, petroleum jelly; synthetic esters and ethers, in particular esters of fatty alcohols, namely; for example, isopropyl myristate, 2-ethylhexyl palmitate, 2-octyldodecyl stearate, isostearyl isostearate; hydroxylated esters such as isostearyl lactate, octyl hydroxystearate, octyldodecyl hydroxystearate, heptanoates, octanoates and decanoates of fatty alcohols; polyol esters such as propylene glycol dioctanoate, neopentyl glycol diheptanoate, diethylene glycol diisononanoate, and pentaerythritol esters; fatty alcohols containing from 12 to 26 carbon atoms such as octyldodecanol, 2-butyloctanol, 2-hexyldecanol, 2-undecylpentadecanol, oleyl alcohol; partially hydrocarbon-based fluoro oils and/or fluorosilicone oils; silicone oils such as volatile or non-volatile, linear or cyclic polymethylsiloxanes (PDMS) that are liquid or semisolid at room temperature such as cyclomethicones and dimethicones, optionally comprising a phenyl group, for instance phenyl trimethicones, siloxanes, and mixtures thereof. These oils are usually present in an amount of 0 to about 90 wt. %, preferably from about 1 to 80 wt. % by weight of the oil phase.

The oil phase of the composition of the invention may also comprise one or more cosmetically acceptable organic solvents. These solvents are present in an amount of 0 to about 60 wt. %, preferably about 1 to 30 wt. % by weight of the composition and can be selected from the group consisting of lipophilic organic solvents, amphiphilic organic solvents and mixtures thereof. Suitable solvents which can be used in the composition of the invention include acetic acid esters such as methyl, ethyl, butyl, amyl or 2-methoxyethyl acetate; isopropyl acetate; hydrocarbons such as toluene, xylene, p-xylene, hexane or heptane; ethers containing at least 3 carbon atoms, and mixtures thereof.

The composition of the invention may further comprise any ingredient conventionally used in the cosmetic field. These ingredients include preserving agents, aqueous phase thickeners (polysaccharide biopolymers, synthetic polymers) and fatty-phase thickeners, fragrances, hydrophilic and lipophilic active agents, and mixtures thereof. The amounts of these various ingredients are those conventionally used in the cosmetic field to achieve their intended purpose, and range typically from about 0.01 to 20 wt. % by weight of the composition. The nature of these ingredients and their amounts must be compatible with the production of the compositions of the invention.

The composition of the invention may also comprise an additional particulate phase, typically present in an amount of 0 to about 30 wt. % by weight of the composition, preferably from about 0.05 to 20 wt. %, and which can comprise pigments and/or pearlescent agents and/or fillers used in cosmetic compositions.

Pigments can be present in the composition in an amount of 0 to 25 wt. % of the weight of the final composition, and preferably in an amount of 1 to 15 wt. %. Suitable inorganic pigments include titanium oxide, zirconium oxide and cerium oxide, as well as zinc oxide, iron oxide, chromium oxide and ferric blue. Suitable organic pigments include barium, strontium, calcium, and aluminium lakes and carbon black Pearlescent agents can be present in the composition in an amount of 0 to 20% of the total weight of the composition, preferably an amount ranging from 1 to 15%. Suitable pearlescent agents include mica coated with titanium oxide, with iron oxide, or with natural pigment.

Fillers are normally present in an amount of 0 to about 30 wt. % by weight of the composition, preferably about 0.5 to 15 wt. %. Suitable fillers include talc, silica, zinc stearate, mica, kaolin, nylon (in particular orgasol) powder, polyethylene powder, Teflon, starch, boron nitride, copolymer microspheres such as Expancel (Nobel Industrie), Polytrap (Dow Coming), and silicone resin microbeads (Tospearl from Toshiba).

The oil phase of the compositions of the invention may comprise one or more waxes, gums, or mixtures thereof. The waxes include hydrocarbon-based waxes, fluoro waxes and/or silicone waxes and can be of plant, mineral, animal and/or synthetic origin. In particular, the waxes have a melting point of greater than 25° C., preferably greater than 45° C. Suitable waxes include beeswax, carnauba wax, candelilla wax, paraffin wax, microcrystalline waxes, ceresin, ozokerite wax; synthetic waxes such as polyethylene waxes, silicone waxes containing from 16 to 45 carbon atoms. The compositions of the present invention may contain from 0 to about 20 wt. % waxes by weight of the composition.

The gums are generally high molecular weight PDMSs or cellulose gums or polysaccharides and the semisolid materials are generally hydrocarbon-based compounds such as lanolins and derivatives thereof or alternatively PDMSs. The compositions of the present invention may contain from 0 to about 25 wt. % gums by weight of the composition, typically from about 0.1%. to 10 wt. %.

The topical compositions of the present invention can be formulated in any suitable product form. Such product forms include, but are not limited to, aerosol spray, cream, emulsion, solid, liquid, dispersion, foam, gel, lotion, mousse, ointment, powder, patch, pomade, solution, pump spray, stick, and towelette. Product applications include all topical skin care product formulations, color cosmetics, personal care products, hair care products, and topical pharmaceutical products. Compositions of the present invention for use in or as cosmetic, dermatological, or pharmaceutical topical application products can conveniently be prepared by various methodologies well known in the art.

The present topical compositions may include one or more of the following: anesthetics, anti-allergenics, antifungals, antimicrobials, other anti-inflammatory agents, antioxidants, antiseptics, chelating agents, colorants, depigmenting agents, emollients, emulsifiers, exfollients, film formers, fragrances, humectants, insect repellents, lubricants, moisturizers, pharmaceutical agents, photostabilizing agents, preservatives, skin protectants, skin penetration enhancers, sunscreens, stabilizers, surfactants, thickeners, viscosity modifiers, vitamins, or any combinations thereof.

The present compositions provide for products, especially cosmetic products, which alleviate skin irritation. The present invention provides compositions having therapeutically specific and standardized supply of active ingredients alleviating skin irritation by inhibiting I-CAM, IFN-$\gamma$, IL1-$\beta$, IL12, IL6, IL8, IL2, IP10, TNF-$\alpha$ and TNFr2. The present compositions can conveniently be formulated to deliver a consistent level of an ingredient, or blend of ingredients, so that the desired effect of alleviation of skin irritation is achieved.

In a further embodiment, the natural plant material as used herein, also includes "synthetic" extracts, i.e. various combinations of known the natural plant material components and/or constituents that are combined to substantially mimic the composition and/or activity of the natural plant material. Such synthetic extracts are included in the term "natural plant material extract." Most preferably, the synthetic extracts have substantially the same number of active components as a natural plant material. The correspondence of the numerical incidence of actives between the synthetic extracts and the natural plant material may also be described in terms of "percent commonality." The synthetic extract has about 50 percent or more commonality to the chemical composition of a plant or natural extract. In other words, the synthetic extract has about 50 percent or more of the active ingredients found in the plant or a natural extract. More preferably, the chemical composition of the synthetic extract has about 70 percent or more commonality to the chemical composition of a plant or a natural extract. Optimally, a synthetic extract has about 90 percent or more commonality to the chemical composition of a plant or a natural extract. The plant or natural extract for comparison is derived, most preferably, from at least one of the following plants: *Populus nigra, Rhinacanthus nasutus, Sapindus rarak*, and *Thumbergia laurifolia*.

For use in the compositions of this invention, the plants or components and/or active constituents are preferably derived directly from the plants. The components may be in a pure form, a semi-pure form, or unpurified form. In a preferred embodiment, the components are in the form of an extract obtained by organic solvent extraction by standard methods known in the art.

Briefly, the organic solvent extraction method involves washing and extracting the plant material using an organic solvent. Non-limiting examples of organic solvents include methanol, ethanol, isopropanol, dichloromethane, chloroform, hexane, xylene, and petroleum ether. An extracting machine may be used for organic solvent extraction as is well known in the field.

Organic solvent extraction involves collecting the raw materials from the plant that contain the desired constituent(s), such as seeds, needles, leaves, roots, bark, cones, stems, rhizomes, callus cells, protoplasts, organs and organ systems, and meristems. These plant materials are ground to small particle sizes, and then put into an extracting machine through an inlet for the raw materials by a measurable charging machine. The plant raw material is pushed in the extracting machine by a thruster, and slowly moves the plant raw material forward. Organic solvent (e.g., ethanol) may be added into the machine through a solvent inlet at the top of a waste discharge outlet. Due to the difference in gravity and equilibrium, the solvent flows toward the raw material inlet, soaks the materials and flows out from the opposite side of the solvent inlet. Since the plant materials and the solvent move in opposite directions against each other, the plant materials are constantly immersed in a solution that contains a low-concentration of extract. As a result of equilibrium, high yield of plant constituent(s) may be achieved by continuously extracting the plant material against the low-concentration solution.

An extraction time suitable to extract the plant constituents is used, typically between about 1-8 hours is suitable, and more preferably is between about 2-6 hours, and most preferably is between about 3-5 hours. The temperature of extraction is between about 30° C.-90° C., preferably between about 40° C.-70° C., and more preferably between about 50° C.-60° C. The collected extract is then fine-filtered to remove debris, and may be used directly, or is concentrated, for example by distilling the solvent or by other conventional processing. A typical extract actives content is above about 25%, preferably above 50%, and the extract can also be provided in powder form.

Similarly, aqueous-organic solvent extraction involves initially collecting raw materials from a plant containing the desired alkaloid(s), such as seeds, needles, leaves, roots, bark, cones, stems, rhizomes, callus cells, protoplasts, organs and organ systems, and meristems of the plant, which are ground into small particle sizes. The ground plant material is soaked in aqueous solution that is acidic or alkaline, depending on the solubility and stability of the desired extract under acidic or alkaline (basic) conditions. For extraction under acidic conditions, an acid such as hydrochloric acid or sulfuric acid is added to water, e.g., at a concentration of about 3% (w/v). For extraction under alkaline conditions, an alkali such as sodium hydroxide or sodium carbonate is added to water. The extraction time and temperature of extraction are typically similar to that used in the organic solvent extraction method described above.

The extract is then collected and fine-filtered to remove debris. Alkaline agents (e.g., ammonia) or acidifying agents (e.g., sulfuric acid) may be added to the extract to neutralize the solution by adjusting the pH, depending on the acidity or alkalinity of the collected extract. The aqueous extract may be used directly, concentrated or dried. Alternatively, organic solvent may then be added to the neutralized solution to transfer the extract from an aqueous phase to an organic phase. Examples of such organic solvents include, but are not limited to, ethanol, isopropanol, butanol, pentanol, hexanol and xylene. The extract comprising the transferred extract actives dissolved in organic solvent may be used directly, used as a concentrate, or dried.

Different plants containing different constituents may be mixed and extracted together. This process of mixed extraction may preferably be used for extracting those plants containing constituents having similar solubility in the solvent used for extraction, such as ethanol. The mixture of extracts may be concentrated and stored in an appropriate solvent.

One skilled in the art would recognize that different plants may require different extraction protocols to achieve optimal results. It should also be noted that different plants containing different constituents can be mixed and extracted together. This process of mixed extraction can preferably be used for extracting those plants containing constituents with similar solubility in the solvent used for extraction, such as ethanol. The mixture of extracts can be concentrated and stored in an appropriate solvent.

The present invention further provides the compositions comprising the natural plant materials, or extracts derived therefrom, preferably for topical administration or for targeted delivery without inducing significant irritation. Thus, the inventive compositions are especially suitable for sensitive skin. The compositions are applied to the skin for a period of time sufficient to improve the aesthetic appearance of skin. The compositions are preferably applied topically at least once or twice daily, or more. The daily application is preferably for a period of at least one day, and preferably one week, two weeks, four weeks, or more. The compositions can be formulated into liposomes which can comprise other additives or substances, and/or which can be modified to more specifically reach or remain at a site following administration.

The compositions of the present invention yield improvements to the aesthetic appearance of the skin by treating dermatological aging, especially chronological, actinic, and hormonal aging. These benefits are manifest by one or more of the following: improvement in skin tone, radiance, clarity and/or tautness; improvement in skin firmness, plumpness, suppleness, and/or softness; improvement in skin texture and/or promotion of retexturization; improvement in skin barrier repair and/or function; improvement in appearance of skin contours; restoration of skin luster and/or brightness; improvement in communication among skin cells; increase in skin cell metabolism decreased by aging and/or menopause; improvement in skin moisturization; enhancement of skin thickness; reducing skin sensitivity; and increase in skin resiliency. By reducing irritation and inflammation in the skin, the natural plant materials, or extracts derived therefrom, may also treat, prevent, reduce, ameliorate, and/or eliminate aesthetically displeasing wrinkles, fine lines, scaling, peeling, flaking, redness, dryness, etc. that can arise from aging.

Another particular embodiment of the present invention is directed to the delivery of the described compositions by the use of targeted delivery systems, for example, liposomes, microspheres (see, e.g., U.S. Pat. No. 5,770,222 to Unger et al.), and the like, so that the components and/or active constituents can more readily reach and affect the area of application, e.g., face or neck, or the other area of the skin.

Also, embraced by the present invention are transdermal modes of delivery, such as patches and the like, with or without a suitable penetration enhancers. The methods and compositions embodied by the invention provide a means by which the components can be effectively administered in a transdermal system. Accordingly, a transdermal means of delivering a composition or formulation (often with a penetration enhancing composition) to the skin is that of the transdermal patch or a similar device as known and described in the art. In a preferred method, the application is through a sustained release vehicle, e.g., a topically applied sustained released patch. Preferably, when a topical patch is used, the patch is applied to the desired area for extended period of time. Preferably, the extended period of time is greater than one hour, most preferably the extended period of time is overnight, i.e., when the user is sleeping.

In another preferred embodiment, the topical compositions of the present invention also include at least one of the following: a skin penetration enhancer, an emollient, a skin plumper, an optical diffuser, a sunscreen, an exfoliation promoter, and an antioxidant. Details with respect to these and other suitable cosmetic ingredients can be found in the International Cosmetic Ingredient Dictionary and Handbook, $10^{th}$ Edition (2004), published by the Cosmetic, Toiletry, and Fragrance Association (CTFA), at pp. 2177-2299, which is herein incorporated by reference in its entirety.

An emollient provides the functional benefits of enhancing skin smoothness and reducing the appearance of fine lines and coarse wrinkles. Examples include isopropyl myristate, petrolatum, isopropyl lanolate, silicones (e.g., methicone, dimethicone), or any mixtures thereof. The emollient is preferably present from about 0.1 wt % to about 50 wt % of the total weight of the composition.

A skin plumper serves as a collagen enhancer to the skin. An example of a suitable, and preferred, skin plumper is palmitoyl oligopeptide. Other skin plumpers are collagen and/or glycosaminoglycan (GAG) enhancing agents. The skin plumper is preferably present from about 0.1 wt % to about 20 wt % of the total weight of the composition.

An optical diffuser is a particle that changes the surface optometrics of skin, resulting in a visual blurring and softening of, for example, lines and wrinkles. Examples of optical diffusers that can be used in the present invention include, but are not limited to, boron nitride, mica, nylon, polymethylmethacrylate (PMMA), polyurethane powder, sericite, silica, silicone powder, talc, Teflon, titanium dioxide, zinc oxide, or any mixtures thereof. The optical diffuser is preferably present from about 0.01 wt % to about 20 wt % of the total weight of the composition.

A sunscreen protects the skin from damaging ultraviolet rays. In an illustrative embodiment of the present invention, the sunscreen would provide both UVA and UVB protection, by using either a single sunscreen or a combination of sunscreens. Among the sunscreens that can be employed in the present compositions are avobenzone, cinnamic acid derivatives (such as octylmethoxy cinnamate), octyl salicylate, oxybenzone, titanium dioxide, zinc oxide, or any mixtures thereof. The sunscreen may be present from about 1 wt % to about 30 wt % of the total weight of the composition. The addition of a sunscreen may prevent/reduce the photodegradation of the composition while in the package as well as serve to protect the skin from ultraviolet radiation.

The compositions of the present invention having sunscreen bring about additional improvements to the aesthetic appearance of skin, including at least one of the following: minimizes sunburning, minimizes tanning, and reduces redness.

The present compositions may also have one or more exfoliation promoters. Suitable examples of an exfoliation promoter that can be used in the present compositions include alpha hydroxy acids (AHA); benzoyl peroxide; beta hydroxy acids; keto acids, such as pyruvic acid, 2-oxopropanoic acid, 2-oxobutanoic acid, and 2-oxopentanoic acid; oxa acids as disclosed in U.S. Pat. Nos. 5,847,003 and 5,834,513 (the disclosures of which are incorporated herein by reference); salicylic acid; urea; or any mixtures thereof. The preferred exfoliation promoters are 3,6,9-trioxaundecanedioic acid, glycolic acid, lactic acid, or any mixtures thereof. See also, Dictionary at p. 2205.

When the present invention includes an exfoliation promoter, the composition has about 0.5 wt % to 30 wt %, preferably about 1 wt % to about 15 wt %, more preferably about 4 wt % to about 10 wt %, and most preferably about 4 wt %, of the exfoliation promoter based on the total weight of the composition.

An antioxidant functions, among other things, to scavenge free radicals from skin to protect the skin from environmental aggressors. Examples of antioxidants that may be used in the present compositions include compounds having phenolic hydroxy functions, such as ascorbic acid and its derivatives/esters; beta-carotene; catechins; curcumin; ferulic acid derivatives (e.g. ethyl ferulate, sodium ferulate); gallic acid derivatives (e.g. propyl gallate); lycopene; reductic acid; rosmarinic acid; tannic acid; tetrahydrocurcumin; tocopherol and its derivatives; uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Compositions of the present invention may have an antioxidant preferably from about 0.001 wt % to about 10 wt %, and more preferably from about 0.001 wt % to about 5 wt %, of the total weight of the composition. See also, Dictionary at p. 2184.

The present composition may also have one or more of the following active agents, ingredients or adjuvants: anesthetics, anti-allergenics, antifungals, antiseptics, chelating agents, colorants, demulcents, emollients, emulsifiers, fragrances, humectants, lubricants, moisturizers, pH adjusters, pigment altering agents, preservatives, stabilizers, surfactants, thickeners, viscosity modifiers, vitamins, or any mixtures thereof. The amounts of these various substances are those that are conventionally used in the cosmetic or pharmaceutical fields, for example, they can constitute from about 0.01% to 20% of the total weight of the composition.

Nonlimiting examples of active agents for formulating into the compositions of the present invention include those reagents having an effect on the treatment of wrinkles and/or fine lines, in addition to the natural plant actives as described, such as keratolytic agents, i.e., an active agent having desquamating, exfoliant, or scrubbing properties, or an active agent which can soften the horny layer of the skin. Other examples of anti-wrinkle or anti-fine line active agents include hydroxy acids and retinoids. These agents can be formulated, for example, in amounts of from about 0.0001% to 5% by weight relative to the total weight of the composition.

Suitable hydroxy acids include, for example, glycolic acid, lactic acid, malic acid, tartaric acid, citric acid, 2-hydroxyalkanoic acid, mandelic acid, salicylic acid and alkyl derivatives thereof, including 5-n-octanoylsalicylic acid, 5-n-dodecanoylsalicylic acid, 5-n-decanoylsalicylic acid, 5-n-octylsalicylic acid, 5-n-heptyloxysalicylic acid, 4-n-heptyloxysalicylic acid and 2-hydroxy-3-methylbenzoic acid or alkoxy derivatives thereof, such as 2-hydroxy-3-methyoxybenzoic acid.

Exemplary retinoids include, without limitation, retinoic acid (e.g., all-trans or 13-cis) and derivatives thereof, retinol (Vitamin A) and esters thereof, such as retinol palmitate, retinol acetate and retinol propionate, and salts thereof.

The plant component(s) of the present invention are preferably contained in a cosmetically or dematologically acceptable vehicle, medium, diluent or carrier.

More particularly, the compositions for topical application can be in the form of a protective care composition for the skin, preferably for the face, the neck, the hands, the feet, or other areas of the body. Nonlimiting examples include day creams or lotions, night creams or lotions, sunscreen creams, lotions, or oils, body milks, makeup (a foundation), artificial tanning compositions, depilatories, and patches.

Emulsifiers are typically present in the compositions of the invention in an amount of about 0.1% to 30%, by weight and preferably from about 0.5% to 30% by weight relative to the total weight of the composition. However, not all compositions will necessarily include emulsifiers. See, Dictionary at p. 2276-2285.

The plant-derived materials or extracts exert their effectiveness according to this invention by preferably working at the site of application, e.g., the skin of face, neck, arms, feet, hands, or chest. According to this invention, the constituents, in general, comprise extracts derived from at least one of the following plants: *Populus nigra, Rhinacanthus nasutus, Sapindus rarak*, and *Thumbergia laurifolia*. Prior to the present invention, these materials were not previously known or recognized to inhibit I-CAM, IFN-γ, IL1-β, IL12, IL6, IL8, IL2, IP10, TNF-α and TNFr2, thereby reducing skin irritation, inflammation, and/or discomfort, that can arise from any condition including, but not limited to, the use of cosmetic products.

In general, for the purposes of the present invention, a substance, such as a natural plant material, or extract derived therefrom, of the described compositions, is recognized as treating skin irritation when it reduces or improves any visible or subjective sign of irritation, inflammation, and/or discomfort, and/or exhibits an inhibitory effect on I-CAM, IFN-γ, IL1-β, IL12, IL6, IL8, IL2, IP10, TNF-α and TNFr2. Reduction of skin irritation and inflammation also serves to smooth out the landscape, or microrelief, of the skin, thereby effecting the prevention, amelioration, reduction, and/or eradication of roughness and/or fine wrinkles in the skin, etc caused by environmental or chemical irritants.

In one embodiment, the present invention relates to the administration of an effective amount of at least natural plant material, or extract derived therefrom, or composition comprised thereof to inhibit at least one cytokine in the skin. In a preferred embodiment, the cytokine is I-CAM, IFN-γ, IL1-β, IL12, IL6, IL8, IL2, IP10, TNF-α and TNFr2, or any combination thereof.

In another embodiment, the present invention encompasses a method of treating skin irritation, inflammation and/or any visible or subjective sign of discomfort, and/or other dermatological effects of aging, comprising applying to skin a composition containing a natural plant material, or extract derived therefrom, in a cosmetically and/or dermatologically acceptable medium, and in an amount effective to treat, reduce, prevent and/or ameliorate the skin irritation, inflammation and/or any visible or subjective sign of discomfort, and/or other dermatological effects of aging. In the method the natural plant is preferably a member of the following: *Populus nigra, Rhinacanthus nasutus, Sapindus rarak*, and *Thumbergia laurifolia* or a combination thereof. The application of the plant containing composition is preferably topical. In addition, the composition is preferably applied via a directed mode of delivery, for example, by topical application of an aqueous composition, liposome, microcapsule, or transdermal patch.

Another embodiment of the present invention relates to a method of improving the aesthetic appearance of skin and comprises applying to the skin, or introducing via a directed mode of delivery, a composition including one or more natural plant materials, or extracts derived therefrom, in an amount effective to improve the aesthetic appearance of the skin. According to this embodiment, the improvement in aesthetic appearance involves the treatment of at least one condition, such as signs of dermatological aging. Dermatological aging can include chronological aging, actinic aging, hormonal aging, or any combination thereof.

As will be appreciated by the practitioner, cosmetic treatments comprising compositions containing the constituents of the invention can be carried out, for example, by topically applying the cosmetic composition as described herein according to the routine technique for administering such compositions. Routine and commonly practiced techniques encompass the application of creams, lotions, gels, sera, ointments, antiperspirants, or deodorants to the skin; spraying as a form of application is also envisioned.

EXAMPLES

The following example describes specific aspects of the invention to illustrate the invention and provide a description of the present methods for those of skill in the art. The example should not be construed as limiting the invention, as the examples merely provide specific methodology useful in the understanding and practice of the invention and its various aspects.

Example 1

Various natural plant extracts of the present invention were evaluated for inhibiting I-CAM, IFN-$\gamma$, IL1-$\beta$, IL12, IL6, IL8, IL2, IP10, TNF-$\alpha$ and TNFr2.

Method Overview 16-pad FAST slides were arrayed in triplicate with 16 anti-cytokine antibodies plus experimental controls using a piezo-electric Perkin Elmer BioChip Arrayer.

Arrayed slides were inspected for integrity.

Arrayed slides were stored dessicated at room temperature until ready for use.

On the day of the analysis, the appropriate number of slides was removed from storage. A 16-pad hybridization was attached to the slides, and the slides were placed onto a FASTframe (4 slides per frame] for processing. Slide processing was carried out according to the following procedure, briefly:

Arrays were blocked for 15 minutes at room temperature using 70 µl S&S Protein Array Blocking buffer.

Blocking buffer was removed and 70 µl of each extract was added to each array. Arrays were incubated for 3 hours at room temperature, with gentle agitation.

Arrays were washed 3 times with Triton Buffered Saline-T (TBS-T).

Arrays were treated with 70 µl of an antibody cocktail, containing one biotinylated antibody corresponding to each of the arrayed antibodies. Arrays were incubated for 1 hour at room temperature, with gentle agitation.

Arrays were washed 3 times with TBS-T.

Arrays were incubated with 70 µl of a solution containing streptavidin-CY5 conjugate for 1 hour at room temperature, with gentle agitation.

Arrays were washed 3 times with TBS-T, quickly rinsed in de-ionized water, and dried.

Slides were imaged in a Perkin-Elmer scanArray 4000 confocal fluorescent imaging system. Array images were saved as 16-bit TIF files, with 10 micron pixel resolution.

Images were analyzed using Imaging Research ArrayVision software. Briefly, spot intensities were determined by subtracting background signal. Spot replicates from each sample condition were averaged and then compared to the appropriate controls. Microsoft Excel and GraphPad Prism were used for additional analysis and data presentation. The results are summarized in Table I.

TABLE I

| Naturals Test battery 2003—Ab MicroArray | ICAM Inhibition | IFN gamma Inhibition | IL 1 beta Inhibition | IL 12p40 Inhibition | IL 12 p70 Inhibition | IL 6 Inhibition |
|---|---|---|---|---|---|---|
| *Thumbergia laurifolia* Linn.—Ethanol Extract | ++ | + | ++ | ++ | ++ | ++++ |
| *Populus nigra* Moench | +++ | + | ++++ | ++ | +++ | +++ |
| *Rhinacanthus nasutus*—hexane extract | ++++ | ++++ | ++++ | ++++ | ++++ | ++++ |
| *Sapindus rarak* A.—ethanol extract | ++ | ++ | + | ++++ | 0 | +++ |

| Naturals Test battery 2003—Ab MicroArray | IL 8 Inhibition | IL2 Inhibition | IP10 Inhibition | TNF alpha Inhibition | TNF r2 Inhibition |
|---|---|---|---|---|---|
| *Thumbergia laurifolia* Linn.—Ethanol Extract | +++ | + | ++++ | +++ | +++ |
| *Populus nigra* Moench | ++++ | + | ++++ | ++++ | ++ |

TABLE I-continued

| | | | | | |
|---|---|---|---|---|---|
| *Rhinacanthus nasutus*—hexane extract | ++++ | +++ | ++++ | ++++ | ++++ |
| *Sapindus rarak* A.—ethanol extract | +++ | ++ | ++++ | +++ | +++ |

Key:
+ 10-20% change
++ 20-40% change
+++ 40-60% change
++++ >60% change
0 No Change The contents of all patents, patent applications, published articles, abstracts, books, reference manuals and abstracts, as cited herein are hereby incorporated by reference in their entireties to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings.

What is claimed is:

1. A topical composition comprising from about 0.001 wt % to about 50 wt % of a plant material or extract of *Thunbergia laurifolia*, an active ingredient present in an amount that would cause skin irritation in the absence of said plant material or extract, and a cosmetically, dermatologically, or pharmaceutically acceptable vehicle, wherein said plant material or extract inhibits I-CAM, IFN-γ, IL1-β, IL12, IL6, IL8, IL2, IP10, TNF-α and TNFr2, and/or any combinations thereof.

2. The composition of claim 1, wherein said plant material or extract is in combination with a plant material or extract of *Rhinacanthus nasutus* and/or *Populus nigra*.

3. The composition of claim 1, wherein said plant material or extract is present in an amount about 0.01 wt % to about 5 wt % based on the total weight of the composition.

4. A method for treating skin irritation, comprising administering to a subject in need of treatment a composition comprising from about 0.001 wt % to about 50 wt % of a plant material or extract of *Thunbergia laurifolia* and a cosmetically, dermatologically, or pharmaceutically acceptable vehicle in an amount effective to ameliorate, reduce, and/or eliminate skin irritation to treat by reducing, ameliorating, inhibiting, alleviating, and/or eliminating signs and results relating to skin irritation, wherein said composition is topically applied to the skin of the face, neck, arms, feet, hands or chest of said subject.

5. The method according to claim 4, wherein said composition is applied for a period of time effective to treat by reducing, ameliorating, inhibiting, alleviating, and/or eliminating signs and results relating to skin irritation, inflammation, and/or subjective discomfort.

6. The method according to claim 4, wherein the composition is applied at least once daily for at least one week.

7. The method according to claim 4, wherein the composition further includes an ingredient selected from the group consisting of an alpha hydroxy add, an oxa add, an oxa diacid, a retinoid, an insect repellent, and a fragrance.

8. The method according to claim 4, wherein the composition is applied to the face and the plant extract inhibits at least one cytokine in the skin, thereby reducing skin irritation.

9. A method of improving the aesthetic appearance of irritated skin, comprising topically applying to the irritated skin of the face, neck, arms, feet, hands or chest, a composition comprising from about 0.001 wt % to about 50 wt % of a plant material or extract of *Thunhergia laurifolia* and a cosmetically, dermatologically, or pharmaceutically acceptable vehicle in an amount effective to improve the aesthetic appearance of irritated skin.

10. The method according to claim 9, wherein the improvement in aesthetic appearance is selected from the group consisting of improvement in skin tone, radiance, clarity and/or tautness; improvement in skin firmness, plumpness, suppleness, and/or softness; improvement in skin texture and/or promotion of retexturization; improvement in skin barrier repair and/or function; improvement in appearance of skin contours; restoration of skin luster and/or brightness; improvement in communication among skin cells; increase in skin cell metabolism decreased by aging and/or menopause; improvement in skin moisturization; enhancement of skin thickness; reducing skin sensitivity; and increase in skin resiliency.

11. The method according to claim 9, wherein the irritated skin is sensitive skin.

12. The method according to claim 9, wherein the composition is applied topically at least once daily for at least one week.

* * * * *